United States Patent

Guena et al.

[11] Patent Number: 5,976,185
[45] Date of Patent: Nov. 2, 1999

[54] INTRAORBITAL SPHERULE

[75] Inventors: Nicolas Guena, Suresnes; Sylvain Auvert, Boulogne Billancourt; Christophe Chaput, Limoges, all of France

[73] Assignee: F.C.I. (France Chirurgie Instrumentation) S.A., Issy-Les-Moulineaux, France

[21] Appl. No.: 09/068,266
[22] PCT Filed: Sep. 10, 1997
[86] PCT No.: PCT/FR97/01590
    § 371 Date: May 5, 1998
    § 102(e) Date: May 5, 1998
[87] PCT Pub. No.: WO98/10715
    PCT Pub. Date: Mar. 19, 1998

[30] Foreign Application Priority Data

Sep. 11, 1996 [FR] France .................................... 96 11066

[51] Int. Cl.[6] ...................................................... A61F 2/14
[52] U.S. Cl. .................... 623/4; 623/4; 623/11; 623/66
[58] Field of Search ...................... 623/4, 11, 66

[56] References Cited

U.S. PATENT DOCUMENTS

| 2,688,139 | 9/1954 | Jardon ........................................... 3/13 |
| 4,000,525 | 1/1977 | Klawitter et al. ......................... 3/1.911 |
| 4,976,731 | 12/1990 | Perry ........................................... 623/4 |
| 5,282,851 | 2/1994 | Jacob-LaBarre ........................... 623/6 |
| 5,549,123 | 8/1996 | Okuyama et al. ....................... 128/898 |
| 5,804,263 | 9/1998 | Goldberg et al. ....................... 428/34.7 |

FOREIGN PATENT DOCUMENTS 9107930  6/1991  Germany ......................... A61F 2/14

*Primary Examiner*—Mickey Yu
*Assistant Examiner*—Dinh X. Nguyen
*Attorney, Agent, or Firm*—Duane Morris & Heckscher, LLP

[57] ABSTRACT

An intra-ocular ball for constituting a prosthesis after enucleation or evisceration of an eye is made of porous sintered alumina having interconnected pores with a diameter of about 300 microns, and capable of receiving a driver after colonization.

5 Claims, 1 Drawing Sheet

INTRAORBITAL SPHERULE

The present invention relates to a ball that is to constitute an implant or prosthesis for replacing the eyeball after enucleation or evisceration.

BACKGROUND OF THE INVENTION

During an enucleation operation the entire eyeball is extracted from the orbital cavity. In evisceration, only the contents of the eyeball is extracted, the scleral shell remaining in place.

In both cases, in order to avoid leaving an empty orbital cavity, it has been known for along time to insert a synthetic prosthesis of spherical shape corresponding to the shape of the normal eye, either directly into the orbital cavity after enucleation or into the scleral shell after evisceration.

On the front of this synthetic prosthesis there is placed that which is commonly called a "glass eye", which in fact, is constituted by a plastic half-shell on which an iris and a pupil are marked, with the shell serving an esthetic purpose only.

The problem posed by such prior prostheses stems from being made of a material that is biocompatible but not colonizable, such as plastic (PMMA) or silicone, thus not enabling the prosthesis to be connected to the half-shell.

It is also known to make an intra-orbital implant comprising a silicone core covered in a biocolonizable material such as expanded PTFE. The drawback of such a prosthesis is that colonization can take place only at the periphery where the biocolonizable material is to be found thus likewise making it impossible to establish a connection between such an implant and the plastic shell.

In patent U.S. Pat. No. 4 976 731 (Perry), it is proposed to make the ball out of sterile porous hydroxyapatite ceramic obtained either from coral or by synthesis. The porosity of the hydroxyapatite prosthesis enables the implant to be colonized in its entirety. That colonization makes it possible subsequently to drill a hole into the ball enabling a driver to be inserted connecting the ball to the plastic half-shell. The driver provides better transmission of movements from the ball to the plastic shell, thereby enabling the artificial eye to move in a manner equivalent to the other eye.

Nevertheless, fabricating such an implant presents great difficulty of implementation associated with very high production costs.

That is in addition to the solubility of hydroxyapatite in the organism, which solubility is of the order of 3%, and gives rise to inflammatory reactions.

OBJECT AND SUMMARY OF THE INVENTION

An object of the present invention is to mitigate those drawbacks and to enable the cost of such implants to be reduced and to propose a material that is highly innocuous, and much more stable over time.

According to the invention, the intra-orbital ball suitable for replacing the eye in the event of enucleation or evisceration is made of a porous sintered metal ceramic.

BRIEF DESCRIPTION OF THE DRAWING

Other characteristics and advantages of the invention appear from the following description given purely by way of non-limiting example and with reference to the sole FIGURE which is a diagram of an implant of the invention.

MORE DETAILED DESCRIPTION

Figure 1:
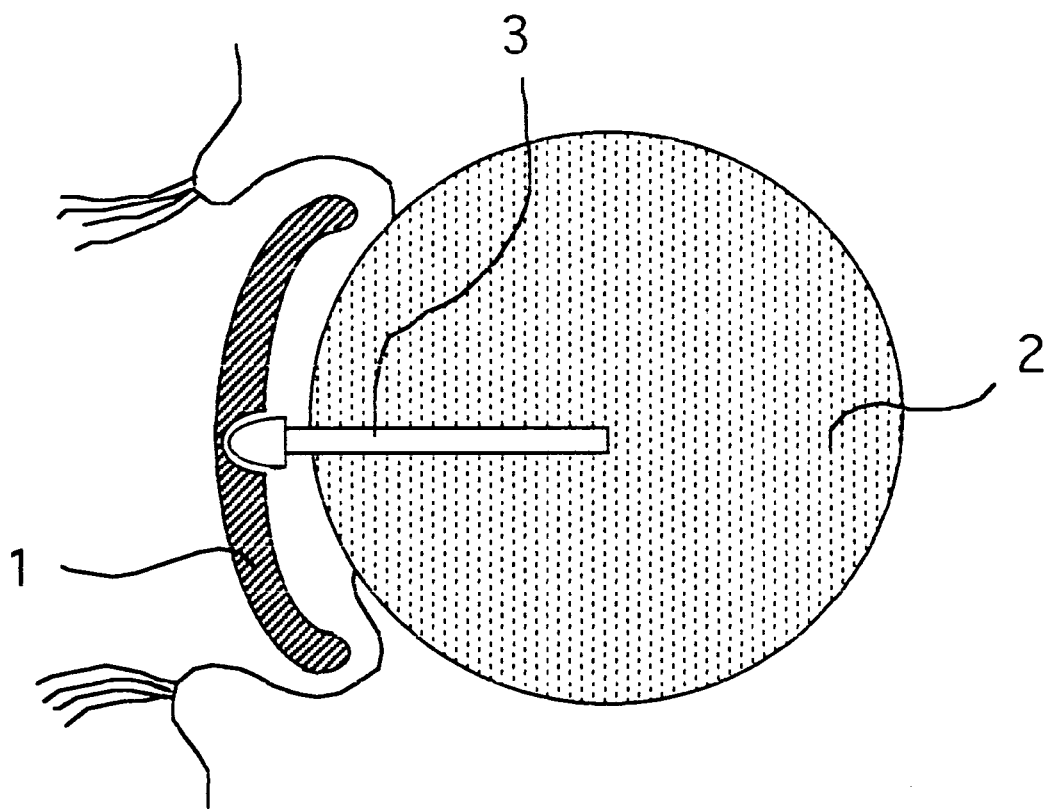

In the figure, there can be seen the colonizable porous ball 2 on which a half-shell 1 is fixed by means of a driver 3 constituted by a rod having one end fixed inside the ball and having its other end pivoted to the half-shell.

The ball is preferably made from sintered metal oxide powder having pores that are fully interconnected and of substantially constant section. Optimum colonization appears to be obtained with pores of about $300\mu$, however colonization can occur with pores that are much smaller or much larger. Once the organism has colonized the ball, it can be drilled to receive the driver 3 in the same manner as a ball made of hydroxyapatite.

The metal ceramic is preferably constituted by alumina in powder form, with a sintering additive incorporated therein and constituting about 1% by weight, e.g. magnesium oxide (MgO).

In addition, alumina is widely available on the market in the ultrapure stoichiometric state, it is absolutely inert both chemically and biologically, and no solubility has been observed. In addition, sintered alumina has very great mechanical strength.

The sintered alumina is prepared from a synthetic foam and an alumina powder of determined grain size. The foam is impregnated with a slip and it is subjected to sintering. The heating melts the plastic and causes the alumna to agglomerate, while leaving the channels or pores of the foam in place. The diameter of the resulting pores is a function of the pores in the original foam.

A drawback that could be presented by a sintered alumina ceramic lies in its very great mechanical strength which makes it difficult to drill. Nevertheless, this problem can be resolved with porous alumina by using a sintering additive such as magnesium oxide (MgO) at a concentration of about 1% by weight, since that makes it possible to reduce the sintering temperature by about 100° C. (1500° C. instead of 1600 ° C.), thereby degrading the mechanical properties of the alumina and making it easier to drill with a drill and a hexagonal milling cutter.

We claim:

1. An intra-orbital ball comprising an implant shaped, sized and configured to be implanted after enucleation or evisceration, said ball having at least a substrate made of a porous sintered metal ceramic.

2. A ball according to claim 1, wherein the ceramic is based on alumina powder.

3. A ball according to claim 1, wherein the pores of the ceramic are interconnected and not closed, having a diameter of about 300 microns.

4. A ball according to claim 2, wherein a sintering additive is mixed with the alumina powder at a concentration of 1% by weight.

5. A method of fabricating a ball according to claim 1, comprising in soaking a foam sphere in an alumina slip and then subjecting said sphere and slip to heating that eliminates the foam.

* * * * *